United States Patent

Schulze et al.

[11] Patent Number: 4,794,119
[45] Date of Patent: Dec. 27, 1988

[54] AQUEOUS CRYSTALLINE SUSPENSION OF STEROID GLYCOESTERS

[75] Inventors: Paul-Eberhard Schulze; Bernard Acksteiner; Bernd Dusterberg, all of Berlin, Fed. Rep. of Germany

[73] Assignee: Schering Aktiengesellschaft, Berlin and Bergkamen, Fed. Rep. of Germany

[21] Appl. No.: 844,642

[22] Filed: Mar. 27, 1986

[30] Foreign Application Priority Data

Mar. 27, 1985 [DE] Fed. Rep. of Germany ....... 3511588

[51] Int. Cl.$^4$ .......................... A61K 31/56; C07J 1/00
[52] U.S. Cl. ..................... 514/170; 514/178; 514/179; 514/182; 260/397.4; 260/397.45; 260/397.5
[58] Field of Search ............. 260/397.4, 397.45, 397.5; 514/170, 178, 179, 182

[56] References Cited

U.S. PATENT DOCUMENTS 4,119,626 10/1978 Schulze et al. .................... 260/397.4
4,588,718 5/1986 Anderson et al. ................... 514/179

FOREIGN PATENT DOCUMENTS 0129947 1/1985 European Pat. Off. .

OTHER PUBLICATIONS

Chemical Abstracts; vol. 91 (1979) #1813762; Huempel et al.

Primary Examiner—Leonard Schenkman
Assistant Examiner—Joseph A. Lipovsky
Attorney, Agent, or Firm—Millen & White

[57] ABSTRACT

An aqueous crystalline suspension of a 17-tertiary steroid glycoester contains a compound of Formula I

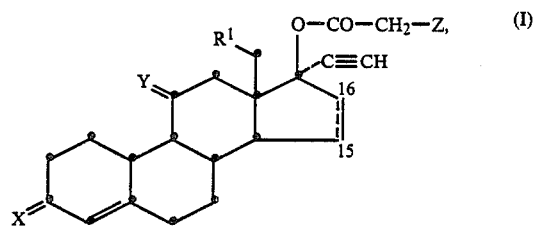

wherein
X is two hydrogen atoms or an oxygen atom,
Y is two hydrogen atoms or a methylene group,
$R^1$ is hydrogen or methyl,
Z is hydroxy or —O—CO—$R^2$
$R^2$ is methyl or phenyl, and $\overset{16}{\underset{15}{\|}}$ is a C—C single or double bond, in the following fractions:
  0–30% by weight of a particle size of 3–15 μm,
  40–90% by weight of a particle size of 15–60 μm, and
  20–60% by weight of a particle size of 30–100 μm.

Upon a one-time intramuscular injection of 30–75 mg of steroid glycoester as an aqueous crystalline suspension, a steroid level is achieved in the plasma which, over a period of 4 weeks, is adequately high and shows a uniform course.

12 Claims, 1 Drawing Sheet

AQUEOUS CRYSTALLINE SUSPENSION OF STEROID GLYCOESTERS

CROSS-REFERENCE TO RELATED APPLICATION

This application is related to U.S. Ser. No. 845,102, filed on Mar. 27, 1986, which disclosure is incorporated by reference herein.

BACKGROUND OF THE INVENTION

This invention relates to aqueous crystalline suspensions of 17-tertiary steriod glycoesters and to glycobenzoates.

The pharmacological activity of steriods lasts only for a short time in general. In order to be used as contraceptives, steriods must be administered daily as a result.

Attempts have been made to prolong their duration of activity by esterification. Thus, it is known that a protractive effect can be achieved by esterifying biologically active steriod alcohols with long-chain, branched or cyclic fatty acids. An additional depot effect is frequently obtained by adding the active agent to a carrier compound that releases the active agent with retardation. One injectable depot contraceptive, for example, is norethisterone enanthate in an oily solution. At a dosage of 200 mg of norethisterone enanthate in 1 ml of castor oil/benzyl benzoate in a ratio of 6:4, the effectiveness lasts about 12 weeks. However, it has been found that the number of pregnancies while under the effect of norethisterone enanthate is somewhat larger than in the case of daily oral ingestion of a tablet. Moreover, undesired pregnancies occur, in particular, shortly before the end of the injection interval.

Investigating the serum steroid concentration after a single intramuscular injection of 200 mg of norethisterone enanthate in human subjects, a high initial concentration or norethisterone has been found. This drops initially very rapidly and then continues to decrease gradually (Contraception 24: 15-17 [1981]). In order to maintain a specific higher level of norethisterone over a period of 12 weeks, it is necessary to administer dosages or norethisterone enanthate that are too high physiologically.

High initial concentrations of medroxyprogesterone have also been measured after injection of medroxyprogesterone acetate as an aqueous crystalline suspension (J. Clin. Endrocinol. Metab. 44: 32-38 [1977]).

Tertiary 17-acylglycol esters are described in German Pat. No. 2,558,076, produced for example, by esterifying the steriod alcohol with glycolic acid and further esterification of the primarily obtained glycol ester with a long-chain carboxylic acid. Another preparation approach is the reaction of the steriod alcohol in one step with the desired acylglycoyl chloride. By interposing glycolic acid, the objective is attained that the tertiary 17-ester, in two stages, is almost completely saponified. The stepwise construction of the ester, however, not only results in an almost complete cleavage of the ester and exploitation of the active agent, but also in a ready availability of the active agent. Directly after injection, a relatively large amount of active agent is released for a few days, which can lead to side effects.

SUMMARY OF THE INVENTION

It is an object of this invention to provide new compounds and/or formulations overcoming or ameliorating these problems.

Upon further study of the specification and appended claims, further objects and advantages of this invention will become apparent to those skilled in the art.

These objects have been achieved by providing aqueous crystalline suspensions of 17-tertiary steriod glycoesters containing a compound of Formula I

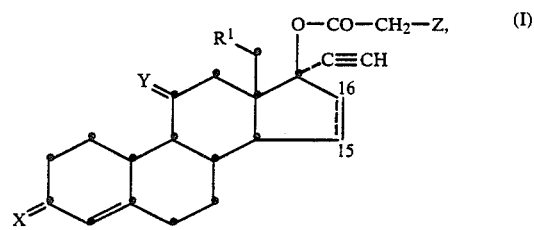

wherein
X is two hydrogen atoms or an oxygen atom,
Y is two hydrogen atoms or a methylene group,
$R^1$ is hydrogen or methyl,
Z is hydroxy or $-O-CO-R^2$
$R^2$ is methyl or phenyl, and $\overset{16}{\underset{15}{||}}$ is a C—C single or double bond, in the following fractions:
0-30% by weight of a particle size of 3-15 μm,
40-90% by weight of a particle size of 15-60 μm, and
20-60% by weight of a particle size of 30-100 μm;
and by providing in another aspect, compounds of Formula Ia

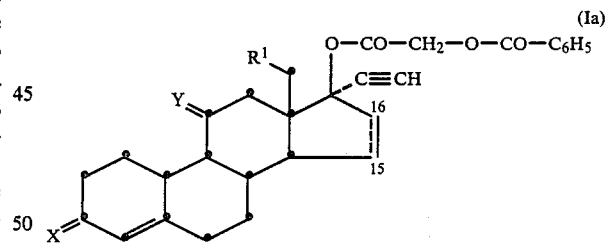

wherein
X is two hydrogen atoms or an oxygen atom,
Y is two hydrogen atoms or a methylene group,
$R^1$ is hydrogen or methyl and $\overset{16}{\underset{15}{||}}$ is a C—C single or double bond.

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein.

DETAILED DESCRIPTION

It has now been discovered that the 17-tertiary steroid glycoesters of Formula I in an aqueous microcrystalline suspension produce upon administration a uniform steroid level which rises slightly toward the middle of the cycle, ensuring a four-week contraceptive effect.

Figure 1:
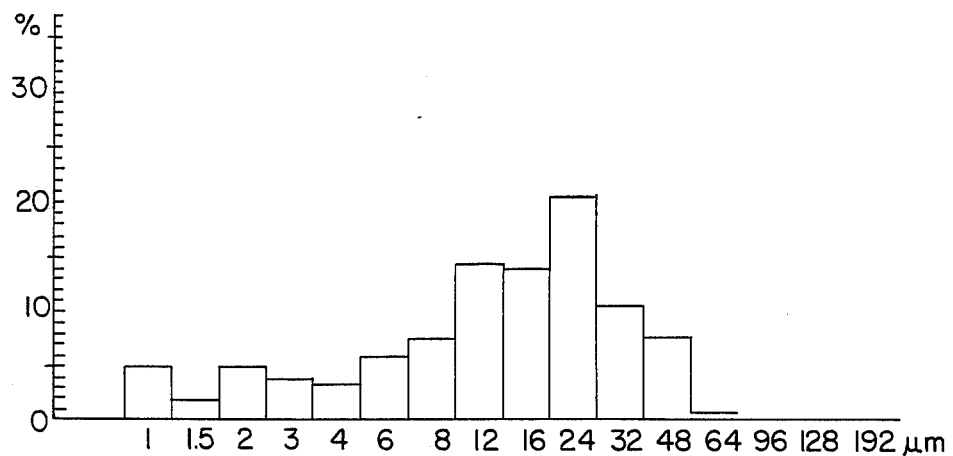
FIG. 1 shows the percentage distribution of crystal sizes in a tested crystalline suspension of norethisterone glycobenzoate.
Figure 2:
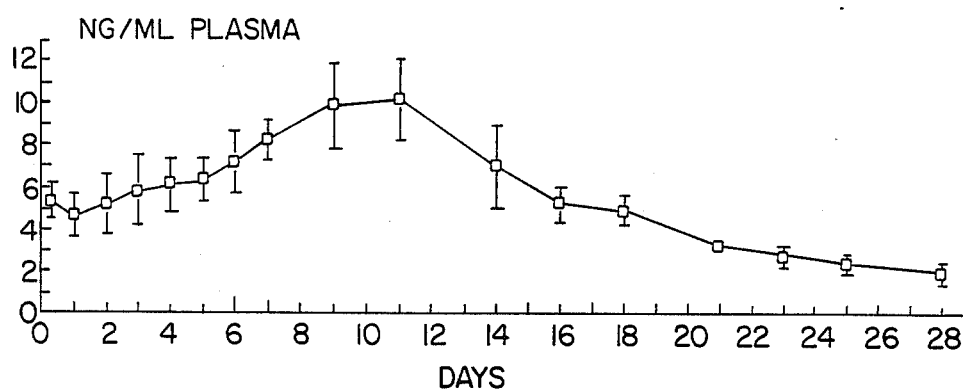
FIG. 2 shows the average norethisterone level after a one-time intramuscular injection of 50 mg of northisterone glycobenzoate in baboons.

A crystalline suspension of 50 mg of norethisterone glycobenzoate, with a distribution of crystal sizes according to the percentages illustrated in FIG. 1, was tested on baboons. After a single intramuscular injection, a norethisterone level was found in the plasma which was adequately high over 4 weeks and showed an extensively uniform curve (FIG. 2). The shape of the curve admits the conclusion that the ester administered is completely released from the depot and is split into norethisterone as well as the natural fatty acids, glycolic acid and benzoic acid. Release of the ester and formation of free norethisterone take place for up to 5 days at almost constant rate, then become slightly greater up to the 11th day, drop gradually down to the initial level up to the 18th day, and reach values, after 28 days, that are so low that withdrawal bleeding occurs. It becomes apparent that it even seems possible to realize, with the tested formulation, the "three-stage concept" of oral contraceptives, using an injection preparation. A limited rise in active agent concentration in the luteal phase can be viewed as advantageous for serving as a "brake" on endogenous hormone secretions including ovulation in the middle of the cycle.

Similar norethisterone levels are obtained with norethisterone glycolate and norethisterone glycoacetate.

Suitable steriods for use in the suspensions of this invention include norethisterone and steriods derived from norethisterone according to Formula I. Preferred base steriods of Formula I are norethisterone, lynestrenol, levonorgestrel, gestodene, or desogestrel.

While the corresponding glycolates and glycoacetates are disclosed in German Pat. No. 2,558,076, the corresponding glycobenzoates are novel.

In order to produce the novel steriod glycobenzoates of Formula Ia, a solution can be made, for example, from 4.56 mmol of the steriod in 7.5 ml of collidine and 7.5 ml of tetrachloroethylene under nitrogen, and the solution can be heated to 120° C. Then within 2 hours, 4.9 mmol of benzoylglycoyl chloride in 10 ml of tetrachloroethylene can be added dropwise thereto. The base is then extracted with oxalic acid solution (from 5 g of oxalic acid), and the solution subsequently extracted by shaking with sodium carbonate solution and water. After drying over sodium sulfate and concentration by means of an oil pump, the residue can be chromatographed on silica gel with methylene chloride/acetone (up to 1% acetone).

For example, 1.36 g of norethisterone and 0.97 g of benzoylglycoyl chloride yield 450 mg of norethisterone glycobenzoate, 17-ethynyl-17-(O-benzoylglycoloyloxy)-4-estren-3-one, which melts at 206°–207° C. after recrystallization from diisopropyl ether.

The base steriods within formula I are well known and/or readily preparable as described in the prior art (e.g., German Pat. No. 2,558,076) or from each other using chemical modifications known in the steriod field.

The ready crystallizability of the 17-tertiary glycoesters covered by Formula I is surprising, since other glycoesters exhibit an unexpectedly low melting point. Crystalline particle distributions useful for preparing particle size fractions useful in conjunction with this invention can be prepared fully conventionally by granulating, crushing, grinding, etc., e.g., using mechanical or other conventional methods, especially ultrasonic treatment, followed by fully conventional screening. Such procedures are well known and described, e.g., in Remington's Pharmaceutical Sciences, 15th Edition 1975, Page, 322, Mack Publishing Company, Easton, Pa.

A microcrystalline suspension of a 17-tertiary steriod glycoester of Formula I can be prepared according to conventional methods and conventionally screened so that three fractions are obtained having the following particle sizes:

(a) 3–15 μm,
(b) 15–60 μm, and
(c) 30–100 μm in approximately linear distribution.

Within each range, the particle distribution is approximately flat, but is not critical.

0–30% by weight of (a)
40–90% by weight of (b), and
20–60% by weight of (c)

are mixed in a fluidized bed for 5 minutes, filled up with physiological sodium chloride solution, optionally with addition of a conventional stabilizer, such as polyoxyethylene stearate ("Myrj 53"), and heat sterilized. The percentages defined for each refer to the total number of particles in the suspension within that range irrespective of whether the particles are also counted as part of another range.

The foregoing weight percentages are based on total weight of steroid. The concentration of steroid of Formula I in the aqueous suspension is usually in the range of 10–200 mg/ml. Other optional ingredients in such suspensions can be included also.

The suspensions and compounds of this invention can be used as a contraceptive component in female mammals, including humans, in conjunction with estrogens in accordance with fully conventional methods and considerations. It is also possible to utilize the suspensions of this invention and the new compounds of this invention in combinations with estrogens for the treatment of gynecological disturbances.

The suspensions of this invention are preferably administered by injection, preferably intramuscularly. Estrogens which can be incorporated in the suspension or which can be administered separately, simultaneously or sequentially, include all conventional estrogens which are well known to those skilled in the art. If the estrogen is not of a long-acting type, it is administered in accordance with conventional procedures. Details are well known. In an especially preferred embodiment, the estrogen will be a long-acting estrogen which can be co-administered with the suspension of this invention over an a long time interval, e.g., preferably only once a month. Such estrogens preferably are those of U.S. Ser. No. 845,102, filed Mar. 27, 1986, discussed above. Generally, the administration of the contraceptive preparations of this invention is analogous to Depo-Clinovir ® and Cyclo-Provera ®.

The one-month single dose effective for contraception for human patients is 20–50 mg of the steriod or, 30–75 mg of the glycoester. In a special embodiment, the long-acting glycoesters of this invention are combined with similar suspensions of long-acting estrogens, especially those of U.S. Ser. No. 845,102, filed Mar. 27, 1986, discussed above.

The one-month single dose of long-acting estrogen which the dose of glycoester of this invention or included in the suspension thereof is 0.5–15 mg of the steroid or, 1–20 mg of the glycoester.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

In an aseptic and pyrogen-free sonic treatment apparatus, 5 g of 17α-ethynyl-17β-(O-benzoylglycoloyoxy)-4-estren-3-one in 50 ml of "Myrj"-sodium chloride solution (0.9% by weight sodium chloride solution with 0.085% by weight of "Myrj") is subjected to sonic treatment for 30 minutes, and the resultant suspension is fractionally screened. Fractions are withdrawn having the following particle sizes:
 (a) 5–15 μm,
 (b) 15–50 μm, and
 (c) 35–50 μm.

In a fluidized bed, 5 g of fractions (a), (b), and (c), in a ratio of 10:50:40, are intermixed and filled up with "Myrj"-sodium chloride solution (0.9% by weight sodium chloride solution with 0.085% by weight of "Myrj") to 100 ml.

EXAMPLE 2

Under the same conditions as in Example 1, 0.5 g of estradiol-17β-benzoyloxyacetate is subjected to sonic treatment for 3 minutes, thus obtaining a particle size distribution of
 (a) 15% by weight of a size of 5–10 μm,
 (b) 60% by weight of a size of 10–26 μm, and
 (c) 25% by weight of a size of 26–40 μm.
See U.S. Ser. No. 845,102, filed Mar. 27, 1986, above.

Fractions (a), (b), and (c) according to Example 1 are suspended with (a), (b), and (c) according to Example 2 in 100 ml of "Myrj"-sodium chloride solution and dispensed under aseptic and sterile conditions into injection kits of respectively 1 ml content. Each injection kit contains
 50 mg: 17α-ethynyl-17β-(O-benzoylglycoloyloxy)-4-estren-3-one and
 5 mg: estradiol-17β-benzoyloxyacetate for intramuscular injection as a 28-day contraceptive (one-month syringe).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An aqueous crystalline suspension comprising an effective amount of a 17-tertiary glycoester of the formula

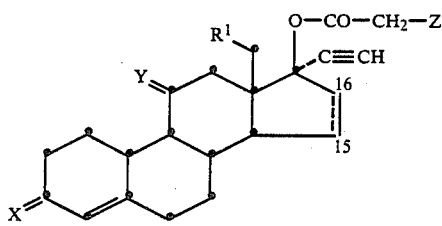

wherein
X is two hydrogen atoms or an oxygen atom,
Y is two hydrogen atoms or a methylene group,
$R^1$ is hydrogen or methyl,
Z is hydroxy or —O—CO—$R^2$,
$R^2$ is methyl or phenyl, and $$\overset{16}{\underset{15}{\|}} \text{ is a C—C single or double bond,}$$

in the following fractions:
 0–30% by weight of a particle size of 5–10 μm,
 40–90% by weight of a particle size of 10–26 μm, and
 20–60% by weight of a particle size of 26–40 μm.

2. A method of achieving a depot effect of a steriod of the formula

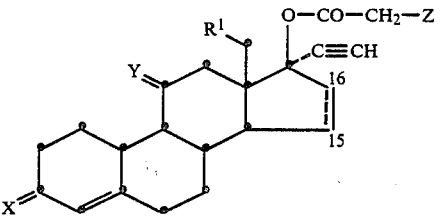

wherein
X is two hydrogen atoms or an oxygen atom,
Y is two hydrogen atoms or a methylene group,
$R^1$ is hydrogen or methyl,
Z is hydroxy or —O—CO—$R^2$,
$R^2$ is methyl or phenyl, and $$\overset{16}{\underset{15}{\|}} \text{ is a C—C single or double bond,}$$

comprising administering an effective amount of the steriod to a patient as an aqueous suspension of claim 1.

3. A method of claim 2, wherein the effect is contraception in a female and further comprising administering an amount of an estrogen effective as a contraceptive.

4. A method of claim 3, wherein the administration of the steriod of said formula is once every 4 weeks.

5. A method of claim 4, wherein the aqueous suspension further comprises an estrogen which also is administered once every 4 weeks.

6. A method of claim 4, wherein the amount of the steriod of said formula is 30-75 mg.

7. A suspension of claim 1, wherein the glycoester is norethisterone glycobenzoate.

8. A suspension of claim 1, wherein the glycoester is the glycoester of norethisterone, lynestrenol, levonorgestrel, gestodene, or desogestrel.

9. A suspension of claim 1, wherein the amount of the glycoester is 30-75 mg.

10. A suspension of claim 1, further comprising an amount of an estrogen effective as a contraceptive.

11. A suspension of claim 10, wherein the estrogen is a long-acting estrogen.

12. A suspension of claim 11, wherein the longacting estrogen is a glycoester of estradiol ($E_2$) or estriol ($E_3$) of general Formula I $$(E_{2,3})-O-CO-CH_2-Z \qquad (I)$$

wherein
Z is hydroxy or —O—CO—R, wherein R is a methyl or phenyl.

* * * * *